(12) United States Patent
Kim et al.

(10) Patent No.: US 8,380,444 B2
(45) Date of Patent: Feb. 19, 2013

(54) METHODS OF MEASURING CONCENTRATION OF COMPONENT IN BIOCHEMICAL SAMPLE AND ESTIMATING RELIABILITY OF TEST RESULT

(75) Inventors: Han Sang Kim, Osan-si (KR); Jung Nam Lee, Incheon (KR); Ji Won Kim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 423 days.

(21) Appl. No.: 12/648,326

(22) Filed: Dec. 29, 2009

(65) Prior Publication Data

US 2010/0174491 A1    Jul. 8, 2010

(30) Foreign Application Priority Data

Jan. 8, 2009 (KR) .................. 10-2009-0001595

(51) Int. Cl.
*G01N 33/48* (2006.01)
(52) U.S. Cl. .......................................... 702/19
(58) Field of Classification Search ............. 702/19
See application file for complete search history.

(56) References Cited

U.S. PATENT DOCUMENTS

| 5,734,468 | A | 3/1998 | McNeal | |
|---|---|---|---|---|
| 6,232,609 | B1 * | 5/2001 | Snyder et al. | 250/461.1 |
| 6,353,471 | B1 | 3/2002 | Samsoondar et al. | |
| 7,248,911 | B2 * | 7/2007 | Jeon et al. | 600/335 |
| 8,204,566 | B2 * | 6/2012 | Schurman et al. | 600/322 |

* cited by examiner

*Primary Examiner* — Aditya Bhat
(74) *Attorney, Agent, or Firm* — Sughrue Mion, PLLC

(57) ABSTRACT

Provided are a method of measuring a concentration of a component in a biochemical sample such as serum, and a method of estimating the reliability of a test result using the method. The method of measuring a concentration of a component includes: preparing plural standard samples having at least one common component which has varying concentrations; measuring absorbances of the component in the standard samples at each of the concentrations for plural light beams having different wavelength bands; determining a regression equation of a relationship between the concentration of the component and the measured absorbances at plural wavelength bands; and applying the regression equation by measuring absorbances at the plural wavelength bands of the biochemical sample and applying the measured plural absorbances of the biochemical sample to the regression equation to calculate the concentration of the component.

16 Claims, 2 Drawing Sheets

METHODS OF MEASURING CONCENTRATION OF COMPONENT IN BIOCHEMICAL SAMPLE AND ESTIMATING RELIABILITY OF TEST RESULT

CROSS-REFERENCE TO RELATED APPLICATIONS

This application claims priority from Korean Patent Application No. 10-2009-0001595, filed on Jan. 8, 2009 in the Korean Intellectual Property Office, the disclosure of which is incorporated herein in its entirety by reference.

BACKGROUND

1. Field

One or more embodiments relate to measuring a concentration of a component in a biochemical sample such as serum, and estimating reliability of a test result using the measuring method.

2. Description of the Related Art

A microfluidic device used in microfluidic operations in which a small amount of fluid is used includes a chamber in which a small amount of fluid can be accommodated, a channel through which the fluid can flow, and a valve for controlling the flow of the fluid.

In order to transport the fluid within the microfluidic device, an operational pressure is needed. Examples of the operational pressure are a capillary pressure or a pressure produced using a pump. Recently, a disk-shaped microfluidic device which drives a fluid by using a centrifugal force generated by rotating the disk-shaped microfluidic device and which includes a chamber and a channel has been proposed. This type of disk-shaped microfluidic device is referred to as a lab compact disk (CD) or a lab-on-a-CD.

The disk-shaped microfluidic device may be used to measure the concentration of a particular component in blood. That is, by separating blood plasma or serum from blood and reacting a reagent that reacts with a particular component in blood with the separated blood plasma or the serum, the concentration of the particular component can be measured based on the reaction result.

Concentrations of several components among various components in blood are known to influence the reliability of the measurement of concentrations of other components of blood. For example, it is known that if the hemoglobin concentration in blood is too high or if there is hemolysis, measurement results of concentrations of components such as lactate dehydrogenase (LD), potassium (K), aspartate aminotransferase (AST), alanine aminotransferase (ALT), etc. are higher than the real values. Components that affect the reliability of concentration measurement of other components are referred to as inhibitors. In addition to hemoglobin, bilirubin and lipid are also known as inhibitors.

These inhibitors may be contained in a biochemical sample, or may be generated when the biochemical sample is extracted. In order to examine the accuracy and reliability of a blood test, concentrations of the inhibitors need to be exactly measured.

SUMMARY OF THE INVENTION

One or more embodiments include an optical method of accurately measuring a concentration of a component in a biochemical sample, and a method of estimating the reliability of a test result using the above method.

According to an aspect of an embodiment, there is provided a method of measuring a concentration of a component in a biochemical sample, the method including: preparing plural standard samples having at least one common predetermined component which has varying concentrations; measuring absorbances of the predetermined component in the standard samples at each of the concentrations for plural light beams having different wavelength bands by emitting the plural light beams having different wavelength bands to the plural standard samples and sensing intensity of the light beams that have passed through the standard samples; determining a regression equation of a relationship between the concentration of the predetermined component and the measured absorbances at plural wavelength bands; and applying the regression equation by measuring absorbances at the plural wavelength bands of the biochemical sample or the diluted biochemical sample and applying the measured plural absorbances of the biochemical sample or the diluted biochemical sample to the regression equation to calculate the concentration of the predetermined component.

The method of measuring a concentration of a component in a biochemical sample includes: preparing n standard samples having at least one common predetermined component which has varying concentrations, where n is a natural number; measuring m×n absorbances of the predetermined component in the n standard samples for m light beams having different wavelength bands by emitting the m light beams to the n standard samples and sensing intensity of the light beams that have passed through the n standard samples; determining a regression equation of the concentration of the predetermined component, in which the absorbances at the m wavelength bands are included as independent variables, by using the measured m×n absorbances; and applying the regression equation by measuring absorbances at the m wavelength bands of the biochemical sample or the biochemical sample that is diluted with distilled water and applying the m absorbances to the corresponding independent variables of the regression equation to calculate the concentration of the predetermined component.

The standard sample may be prepared by diluting the at least one predetermined component with distilled water.

The biochemical sample may contain blood plasma or serum.

The predetermined component in the standard sample may be at least one of hemoglobin, bilirubin, and lipid.

The regression equation of the concentration of the predetermined component may be for the concentration of one of hemoglobin, bilirubin, and lipid.

The regression equation of the concentration of the predetermined component may contain absorbances at ten wavelength bands of 340 nm, 405 nm, 450 nm, 500 nm, 550 nm, 570 nm, 600 nm, 630 nm, 660 nm, and 700 nm as independent variables.

The regression equation of the concentration of the component may be for the lipid concentration and further include a bilirubin concentration as an independent variable, wherein the applying of the regression equation further comprises applying the bilirubin concentration in the biochemical sample or the biochemical sample that is diluted with distilled water as an independent variable of the regression equation.

According to an aspect of another embodiment, there is provided a method of estimating reliability of a test result, the method including: measuring a concentration of a predetermined component in a biochemical sample using the above method; labeling index levels to the measured concentration of the component of the biochemical sample; and estimating reliability of the measurement result of concentrations of other components in the biochemical sample based on the labeled index levels.

BRIEF DESCRIPTION OF THE DRAWINGS

The above and/or other aspects will become apparent and more readily appreciated from the following description of the embodiments, taken in conjunction with the accompanying drawings of which.

DETAILED DESCRIPTION

Figure 1:
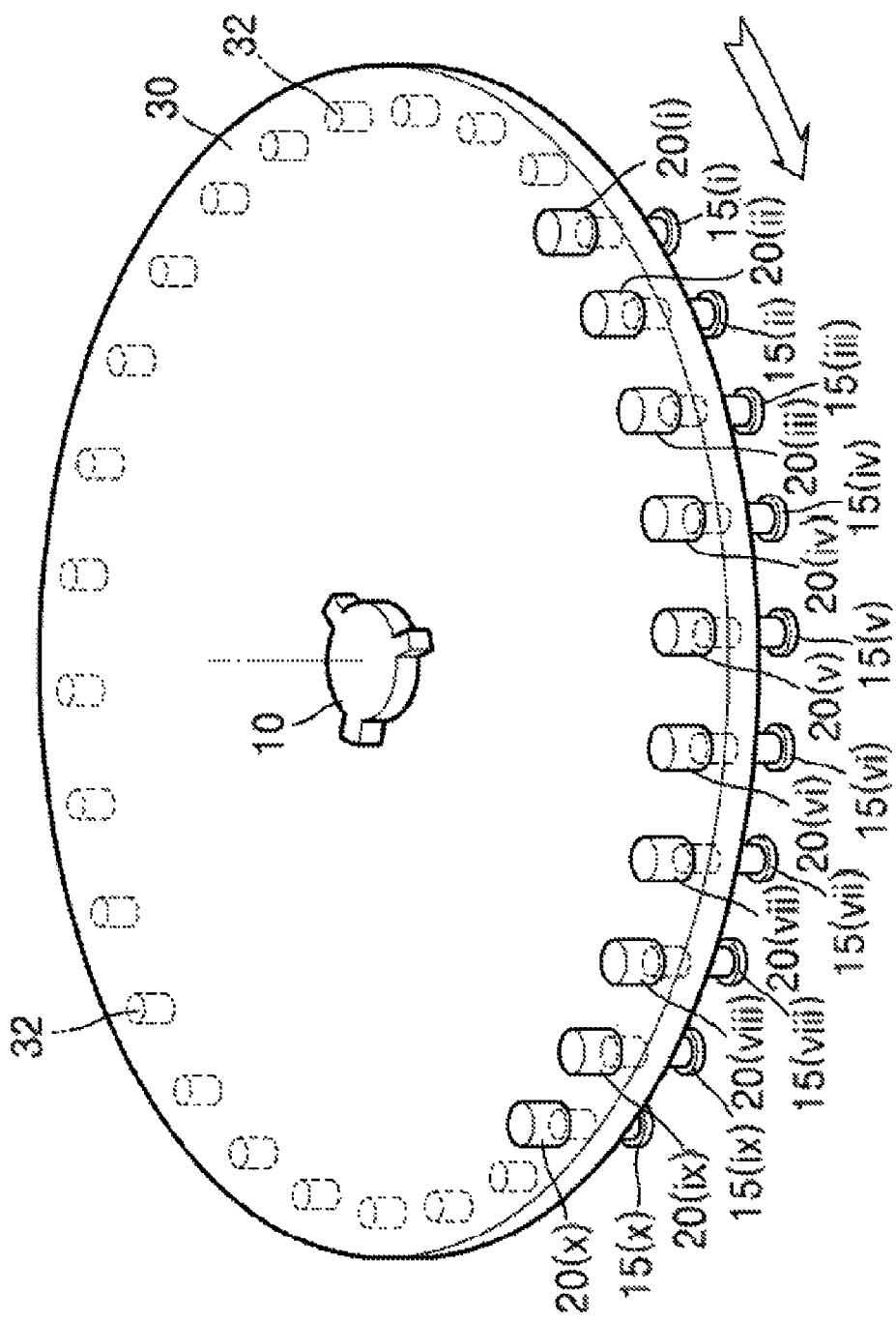
FIG. 1 is a perspective view illustrating an apparatus for measuring absorbances of a plurality of standard samples having components with different concentrations according to an embodiment.

Reference will now be made in detail to embodiments, examples of which are illustrated in the accompanying drawings, wherein like reference numerals refer to the like elements throughout. In this regard, the embodiments may have different forms and should not be construed as being limited to the descriptions set forth herein. Accordingly, the embodiments are merely described below by referring to the figures, to explain aspects of the present description.

A method of measuring a concentration of a component in a biochemical sample according to an embodiment includes providing a standard sample, measuring an absorbance of the standard sample, determining a regression equation, and applying the regression equation.

The standard sample contains at least one particular component whose concentration is known. The standard sample may be formed by diluting the at least one particular component with distilled water. The component may be one of components that affects the measurement reliability of other components among various components in blood. These inhibiting components are referred to as inhibitors. Examples of inhibitors are hemoglobin, bilirubin, and lipid.

Hemoglobin is a component that is measured to examine whether hemolysis is present. When blood is hemolyzed and thus the hemoglobin concentration is high, measurement results of concentrations of other components such as lactate dehydrogenase (LD), potassium (K), aspartate aminotransferase (AST), alanine aminotransferase (ALT), etc. may be higher than the real values. Bilirubin is a component that is measured to examine whether icterus is present. Bilirubin in a too high concentration may interfere in measurement of concentrations of components such as total protein (TP), albumin (ALB), cholesterol (CHOL), creatinine (CRE), uric acid (UA), etc., and increase a difference error between measured concentrations and actual concentrations of other components. Lipid is a component that is measured to examine whether lipemia is present. Lipid in a too high concentration may interfere in measurement of concentrations of components such as albumin (ALB), total bilirubin (TBIL), cholesterol (CHOL), triglyceride (TRIG), etc., and increase a difference error between measured concentrations and actual concentrations of other components.

In the providing of a standard sample, n standard samples having at least one common component varying concentrations are provided. Here, n is a natural number. In the current embodiment, hemoglobin concentration varies from 0 mg/dl, to 100 mg/dl, to 200 mg/dl, bilirubin concentration varies from 5.7 mg/dl, to 15.7 mg/dl, to 25.7 mg/dl, and lipid concentration varies from 203 mg/dl, to 1184 mg/dl, to 4128 mg/dl. Thus, $27(=3^3)$ standard samples with different concentration combinations of hemoglobin, bilirubin, and lipid are provided in total. FIG. 1 is a perspective view illustrating an apparatus for measuring absorbance of the standard samples having at least one common component with different concentrations. In FIG. 1, the apparatus is a disk-shaped microfluidic device 30 according to an embodiment, however, the present invention is not limited thereto.

Referring to FIG. 1, absorbance of the plurality of the standard samples may be measured in a short time using the microfluidic device 30. The microfluidic device 30 may be formed of a plastic material such as polymethyl methacrylate (PMMA), polydimethylsiloxane (PDMS), or polycarbonate (PC), which can be easily molded, is optically transparent, and whose surface is biologically inactive. However, the material for forming the microfluidic device 30 is not limited thereto, and may also be any material that has chemical and biological stabilities, optical transparency, and mechanical processiblity.

A center portion of the microfluidic device 30 may be mounted on a spindle 10 of a motor (not shown) such that the microfluidic device 30 is rotated according to rotation of the spindle 10. The microfluidic device 30 includes a plurality of chambers 32 formed along a circular path with respect to the rotation center of the microfluidic device 30. The plurality of the chambers 32 are arranged at identical intervals.

There are m light sources are disposed below the microfluidic device 30, where m is a natural number. In the current embodiment, m is 10. The ten light sources $15(i)$ through $15(x)$ are arranged at the same intervals as the intervals between the chambers 32, along a circular path with respect to the rotation center of the microfluidic device 30. The ten light sources $15(i)$ through $15(x)$ respectively include light emitting diodes (LEDs) emitting light which may have wavelength bands of 340 nm, 405 nm, 450 nm, 500 nm, 550 nm, 570 nm, 600 nm, 630 nm, 660 nm, and 700 nm.

Ten optical detectors $20(i)$ through $20(x)$ are arranged on or above the microfluidic device 30 to correspond to the ten light sources $15(i)$ through $15(x)$, respectively. The ten optical detectors $20(i)$ through $20(x)$ are also arranged at the same intervals as the intervals between the chambers 32, along a circular path with respect to the rotation center of the microfluidic device 30. Light emitted from the ten light sources $15(i)$ through $15(x)$ having different wavelength bands passes through the microfluidic device 30, and is incident on the corresponding optical detectors $20(i)$ through $20(x)$. The optical detectors $20(i)$ through $20(x)$ include photo diodes. Absorbance can be measured from the intensity of light incident on the optical detectors $20(i)$ through $20(x)$.

For example, in order to measure absorbance of twenty-seven standard samples with different concentration combinations which are known, the twenty-seven standard samples are sequentially injected into twenty-seven chambers from among the chambers 32 of the microfluidic device 30. Then, the microfluidic device 30 is rotated in direction of the arrow (e.g., clockwise), and when one of the chambers 32, that is, a first chamber $32(i)$ containing a standard sample having a predetermined concentration combination is positioned on an optical path between a first light source $15(i)$ and a first optical detector $20(i)$, the rotation is stopped and the first light source $15(i)$ is operated. Absorbance A of light having a wavelength band of 340 nm of the standard sample with the above predetermined concentration combinations may be measured from the intensity of light that is emitted from the first light source $15(i)$ and passes through the first chamber $32(i)$ and is sensed by the first optical detector $20(i)$. The absorbance A may be calculated using Equation 1 below.

$$A = -\log(I/I_0) \quad \text{[Equation 1]}$$

where A is the absorbance, $I_0$ is the intensity of light that passes through pure distilled water, and I is the intensity of light that passes through a fluid.

A total of 270 (m×n=27×10) absorbances of the twenty-seven standard samples with different concentration combinations of hemoglobin, bilirubin, and lipid may be measured by rotating the microfluidic device 30 in the direction of the arrow at an angle corresponding to the interval between two adjacent chambers among the chambers $32(i)$ through $32(x)$, sequentially emitting light from the first through tenth light sources $15(i)$ through $15(x)$ to each of the chambers $32(i)$ through $32(x)$, and sensing light intensity of the emitted light using the optical detectors $20(i)$ through $20(x)$ corresponding to the first through tenth light sources $15(i)$ through $15(x)$. The value 270 is obtained by multiplying m by n, that is, the number m of the light sources $15(i)$ through $15(x)$ having different wavelength bands multiplied by the number n of the standard samples.

The determining of a regression equation determines a regression equation of a relationship between the concentration of the predetermined component and the measured absorbances at plural wavelength bands. More specifically, in the determining of the regression equation, regression equations of concentrations of predetermined components, in which the absorbance at m wavelength bands is included as an independent variable, are calculated using the measured m×n absorbances. The regression equation may be calculated using a statistics analysis program. The regression equation may be a partial least square (PLS) regression equation calculated by PLS analysis.

The regression equations of the concentrations of hemoglobin, bilirubin, and lipid obtained from PLS analysis on data of the 270 absorbances are given by Equations 2 through 4 below.

$HEM=12.26+39.71\times A[340\text{ nm}]+102.65\times A[405\text{ nm}]-166.35\times A[450\text{ nm}]+210.5\times A[500\text{ nm}]-413.22\times A[550\text{ nm}]-538.55\times A[570\text{ nm}]+251.01\times A[600\text{ nm}]+1327.18\times A[630\text{ nm}]-355.22\times A[660\text{ nm}]-1115.44\times A[700\text{ nm}]$ <Equation 2>

$BIL=7.7+76.54\times A[340\text{ nm}]+14.74\times A[405\text{ nm}]-22.73\times A[450\text{ nm}]+34.06\times A[500\text{ nm}]-388.13\times A[550\text{ nm}]-345.91\times A[570\text{ nm}]+1156.49\times A[600\text{ nm}]-1183.93\times A[630\text{ nm}]+509.73\times A[660\text{ nm}]-305.64\times A[700\text{ nm}]$ <Equation 3>

$LIP=-4108+26938\times A[340\text{ nm}]-1259\times A[405\text{ nm}]-20520\times A[450\text{ nm}]+29420\times A[500\text{ nm}]-11517\times A[550\text{ nm}]+74726\times A[570\text{ nm}]+39229\times A[600\text{ nm}]-317555\times A[630\text{ nm}]+160366\times A[660\text{ nm}]+24309\times A[700\text{ nm}]$ <Equation 4>

Here, HEM, BIL, and LIP denote the concentrations of hemoglobin, bilirubin, and lipid, respectively, and A[340 nm], A[405 nm], A[450 nm], A[500 nm], A[550 nm], A[570 nm], A[600 nm], A[630 nm], A[660 nm], and A[700 nm] denote absorbances at wavelength bands of 340 nm, 405 nm, 450 nm, 500 nm, 550 nm, 570 nm, 600 nm, 630 nm, 660 nm, and 700 nm, respectively.

The accuracy of Equation 4, the regression equation of the lipid concentration, may be further increased if the bilirubin concentration is further included as an independent variable as shown in Equation 5 below, in addition to the absorbance at the above ten wavelength bands.

$LIP=-4108+26938\times A[340\text{ nm}]-1259\times A[405\text{ nm}]-20520\times A[450\text{ nm}]+29420\times A[500\text{ nm}]-11517\times A[550\text{ nm}]+74726\times A[570\text{ nm}]+39229\times A[600\text{ nm}]-317555\times A[630\text{ nm}]+160366\times A[660\text{ nm}]+24309\times A[700\text{ nm}]+140\times BIL$ <Equation 5>

In order to examine the reliabilities of Equations 2, 3, and 5, a verification was conducted. For verification, the concentration of the hemoglobin was varied from 0 mg/dl to 100 mg/dl, and the bilirubin concentration was varied from 5.78 mg/dl, to 15.78 mg/dl, and to 25.78 mg/dl, and the lipid concentration was varied from 203 mg/dl, to 1184 mg/dl, and to 4128 mg/dl. Thus, 18 (=2×$3^2$) standard samples with different concentration combinations of hemoglobin, bilirubin, and lipid were prepared in total. Absorbances at wavelength bands of 340 nm, 405 nm, 450 nm, 500 nm, 550 nm, 570 nm, 600 nm, 630 nm, 660 nm, and 700 nm of the standard samples were measured. The measured absorbances were used in Equations 2, 3, and 5 to calculate the concentrations of hemoglobin, bilirubin, and lipid.

The hemoglobin concentration calculated according to Equation 2 was 0.999 on average, while a hemoglobin concentration of an actual standard sample was considered to be equal to 1, and the standard deviation was 0.02. The bilirubin concentration assumed according to Equation 3 was 1.0 on average, while a bilirubin concentration of an actual standard sample was assumed to be equal to 1, and the standard deviation was 0.13. The bilirubin concentration calculated according to Equation 5 was 1.039 on average, while a lipid concentration of an actual standard sample was assumed to be equal to 1, and the standard deviation was 0.209.

Figure 2:
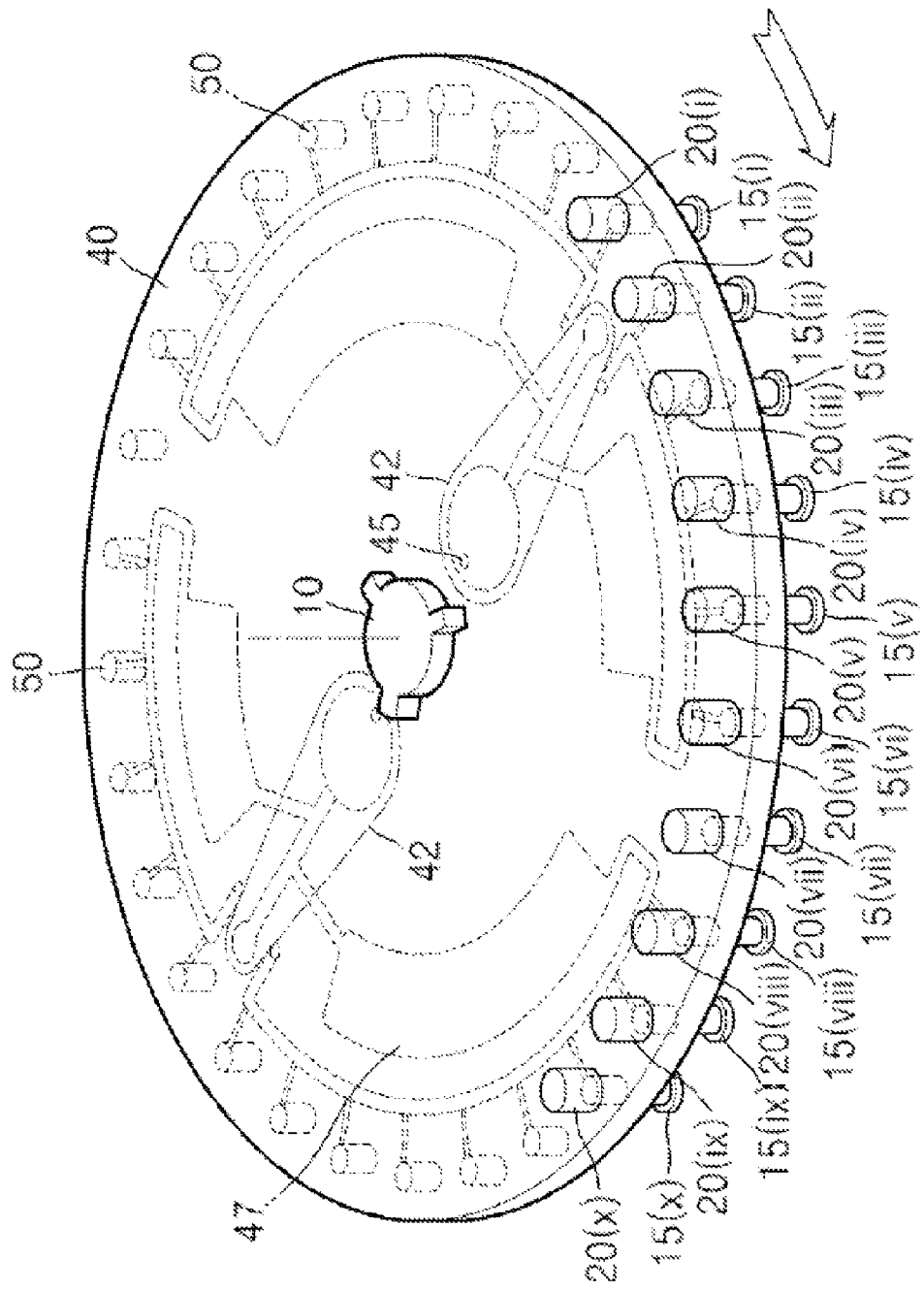
FIG. 2 is a perspective view illustrating an apparatus for measuring a concentration of a component in a biochemical sample using an optical method according to an embodiment.

FIG. 2 is a perspective view illustrating an apparatus for measuring a concentration of a predetermined component in a biochemical sample using an optical method, according to another embodiment.

The above-described regression equations may be applied in the case of the microfluidic device 40 illustrated in FIG. 2, which has a different disk shape from the microfluidic device 30 of FIG. 1. The microfluidic device 40 is designed to examine various blood test items at the same time. Similar to the microfluidic device 30 of FIG. 1, the microfluidic device 40 of FIG. 2 may be formed of a plastic material such as (PMMA, PDMS, or PC. A center portion of the microfluidic device 40 is mounted in a spindle 10 of a motor (not shown) such that the microfluidic device 40 is rotated according to rotation of the spindle 10. The microfluidic device 40 includes a centrifugal unit 42, a sample chamber 47, and a plurality of detection chambers 50.

The centrifugal unit 42 is for separating blood plasma or serum from blood by using a centrifugal force, and includes an injection hole 45 through which the blood is injected into the centrifugal unit 42. The sample chamber 47 is a chamber in which the centrifuged blood plasma or serum is collected. The blood plasma or the serum is a biochemical sample for testing blood. The blood plasma refers to the liquid component of blood from which enthrocyte, leucocyte, and plaque deposits are eliminated. The blood plasma contains fibrinogen. The serum refers to the blood plasma without fibrinogen.

The blood plasma or the serum collected in the sample chamber 47 is moved through a channel to the plurality of detection chambers 50 disposed on an outer circumferential portion of the microfluidic device 40. The centrifugal operation, the transportation of the biochemical sample from the centrifugal unit 42 to the sample chamber 47, and the transportation of the biochemical sample from the sample chamber 47 to the detection chambers 50 are caused by a centrifugal force generated by rotation of the microfluidic device 40. A valve (not shown) may be provided in the channel to control the movement of the serum. Similar to the chambers 32 in FIG. 1, the plurality of the detection chambers 50 are disposed along a circular path with respect to the rotation center of the microfluidic device 40 and at identical intervals. Ten light sources 15(*i*) through 15(*x*) and ten optical detectors 20(*i*) through 20(*x*), which are the same as those described with reference to FIG. 1, may be arranged on and below the microfluidic device 40, respectively. When the blood injected through the injection hole 45 into the centrifugal unit 42 is centrifuged, a biochemical sample such as blood plasma or serum is accommodated in the sample chamber 47, and the biochemical sample is pressurized by a centrifugal force and is transported to the detection chambers 50. Although not illustrated in FIG. 2, a diluent chamber accommodating distilled water for diluting the biochemical sample may be further included in the microfluidic device 40. In this case, a biochemical sample which is diluted using distilled water is accommodated in the detection chambers 50.

When the microfluidic device 40 is rotated such that the detection chambers 50 accommodating the biochemical sample pass through between all of the ten light sources 15(*i*) through 15(*x*) and the ten optical detectors 20(*i*) through 20(*x*), concentrations of predetermined components in the biochemical sample such as hemoglobin, bilirubin, and lipid can be calculated. In detail, the microfluidic device 40 is rotated in the direction of the arrow (clockwise), and when one of the detection chambers 50 containing the biochemical sample is positioned on an optical path between a first light source 15(*i*) and a first optical detector 20(*i*), the rotation is stopped and the first light source 15(*i*) is operated. Absorbance A at a wavelength band of 340 nm of the biochemical sample accommodated in the detection chamber 50 may be measured from the intensity of light that is emitted from the first light source 15(*i*) and passes through the detection chamber 50 and is sensed by the first optical detector 20(*i*). The absorbance A may be calculated using Equation 1.

Absorbances of the biochemical sample at wavelength bands of 340 nm, 405 nm, 450 nm, 500 nm, 550 nm, 570 nm, 600 nm, 630 nm, 660 nm, and 700 nm may be measured by rotating the microfluidic device 40 in the direction of the arrow at an angle corresponding to an interval between two adjacent detection chambers among the detection chambers 30, and sequentially emitting light from the first through tenth light sources 15(*i*) through 15(*x*) to each of the detection chambers 50, and sensing light intensity of the emitted light incident on the optical detectors 20(*i*) through 20(*x*) corresponding to the first through tenth light sources 15(*i*) through 15(*x*).

The hemoglobin concentration may be calculated by inserting the measured ten absorbances in Equation 2, and the bilirubin concentration may be calculated by inserting the measured ten absorbances in Equation 3. Also, the lipid concentration may be calculated by inserting the measured ten absorbances and the bilirubin concentration in Equation 5. A method of estimating the reliability of test results according to an embodiment includes measuring concentrations of predetermined components in a biochemical sample using the above methods described with reference to FIGS. 1 and 2, labeling index levels to the measured concentrations of the predetermined components, and estimating the reliability of the measurements of concentrations of other components in the biochemical sample according to the labeled index levels.

For example, index levels may be labeled to the concentrations of hemoglobin, bilirubin, and lipid, which are inhibitors, as shown in Table 1.

TABLE 1

| Component | Concentration [mg/dl] | Index label |
|---|---|---|
| Hemoglobin | 0~50 | Level 1 |
|  | 51~100 | Level 2 |
|  | 101~150 | Level 3 |
|  | 151~200 | Level 4 |
| Bilirubin | 0~6.0 | Level 1 |
|  | 6.1~12 | Level 2 |
|  | 12.1~18 | Level 3 |
|  | 18.1~24 | Level 4 |
|  | 24.1~30 | Level 5 |
| Lipid | 0~450 | Level 1 |
|  | 451~900 | Level 2 |
|  | 901~1350 | Level 3 |

For example, if a measured hemoglobin concentration is 150 mg/dl, the biochemical sample has a hemoglobin index level Level 3. As described above, when the hemoglobin concentration in the blood is high, concentrations of components such as LD, K, AST, or ALT may be measured higher than the real values. Accordingly, it can be presumed that the concentrations of LD, K, AST, or ALT measured using a biochemical sample of Level 3 may have lower reliability than a measurement result obtained using a biochemical sample of Level 1 or Level 2, and may have higher reliability than a measurement result obtained using a biochemical sample of Level 4.

The labeling of index levels to the measured bilirubin concentration or the measured lipid concentration and the estimating of the reliability of the measurements of other components according to the labeled index levels are performed in the same manner as in the above-described case of hemoglobin, and thus description thereof will not be repeated.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A method of measuring a concentration of a component in a biochemical sample, the method comprising:

injecting a plurality of standard samples into a plurality of chambers of a first centrifugal microfluidic device, wherein the plurality of standard samples includes at least one common component, and each of the plurality of standard samples has a different concentration of the component;

measuring absorbances of the component in each of the plurality of standard samples contained in the chambers of the centrifugal microfluidic device at a plurality of different wavelength bands by emitting from a plurality of light sources a plurality of light beams having the plurality of wavelength bands to the plurality of standard samples and sensing by a plurality of optical detectors intensities of the plurality of light beams that have passed through the plurality of standard samples;

determining a regression equation of a relationship between the concentration of the component and the measured absorbances of the component in the plurality of standard samples at the plurality of wavelength bands; and measuring absorbances of the biochemical sample contained in a plurality of chambers of a second centrifugal microfluidic device at the plurality of wavelength bands by emitting from the plurality of light sources the plurality of light beams having the plurality of wavelength bands to the biochemical sample and sensing by the plurality of optical detectors intensities of the plurality of light beams that have passed through the biochemical sample and applying the measured absorbances of the biochemical sample to the regression equation to calculate the concentration of the component in the biochemical sample.

2. The method of claim 1, wherein the determining the regression equation comprises determining the regression equation of the concentration of the component, in which the absorbances of the component in the plurality of standard samples at the plurality of wavelength bands are included as independent variables, based on the measured absorbances of the component in the plurality of standard samples.

3. The method of claim 2, wherein the applying the regression equation comprises applying the absorbances of the biochemical sample measured at the plurality of wavelength bands to corresponding independent variables of the regression equation to calculate the concentration of the component in the biochemical sample.

4. The method of claim 3, wherein a number of the standard samples in the injecting the plurality of standard samples is n, and n is a natural number;
wherein a number of the plurality of wavelength bands is m, a number of the measured absorbances is m×n in the measuring absorbances, and m is a natural number;
wherein the regression equation includes the absorbances at the m wavelength bands as independent variables in the determining the regression equation; and
wherein the measured absorbances of the biochemical sample are the absorbances at the m wavelength bands, and the m absorbances are applied to the corresponding independent variables of the regression equation in the applying the regression equation.

5. The method of claim 2, wherein the regression equation of the concentration of the component further includes a concentration of another component as an independent variable; and
wherein the applying of the regression equation further comprises applying the concentration of the other component in the biochemical sample to an corresponding independent variable of the regression equation.

6. The method of claim 2, wherein the regression equation of the concentration of the component is for the lipid concentration, and further includes a bilirubin concentration as an independent variable, and
wherein the applying the regression equation further comprises applying the bilirubin concentration in the biochemical sample to an corresponding independent variable of the regression equation.

7. The method of claim 1, wherein the standard sample is prepared by diluting the at least one component with distilled water.

8. The method of claim 1, wherein the biochemical sample contains blood plasma or serum.

9. The method of claim 1, wherein the component is at least one of hemoglobin, bilirubin, and lipid.

10. The method of claim 1, wherein the regression equation is for the concentration of one of hemoglobin, bilirubin, and lipid.

11. The method of claim 1, wherein the regression equation includes absorbances at wavelength bands of 340 nm, 405 nm, 450 nm, 500 nm, 550 nm, 570 nm, 600 nm, 630 nm, 660 nm, and 700 nm as independent variables.

12. The method of claim 1, wherein the biochemical sample is a diluted biochemical sample.

13. A method of estimating reliability of a test result, the method comprising:
measuring a concentration of a predetermined component in a biochemical sample using the method of claim 1;
labeling index levels to the measured concentration of the component of the biochemical sample; and
estimating reliability of the measurement result of concentrations of other components in the biochemical sample based on the labeled index levels.

14. The method of claim 1, further comprising, prior to the measuring the absorbances of the biochemical sample, injecting the biochemical sample into the second centrifugal microfluidic device and rotating the second centrifugal microfluidic device so as to move the biochemical sample into the plurality of chambers.

15. A method of measuring a concentration of a component in a biochemical sample, the method comprising:
injecting n standard samples having at least one common component into a plurality of chambers of a centrifugal microfluidic device, wherein each of the n standard samples has a different concentration of the component and n is a natural number;
measuring m×n absorbances of the component in the n standard samples contained in the chambers of the centrifugal microfluidic device at m wavelength bands by emitting from a plurality of light sources m light beams each having a different wavelength band of the m wavelength bands to the n standard samples and sensing by a plurality of optical detectors intensities of the m light beams that have passed through the n standard samples;
determining a regression equation of the concentration of the component, in which the absorbances at the m wavelength bands are included as independent variables, based on the measured m×n absorbances; and
measuring absorbances of the biochemical sample contained in a plurality of chambers of a second centrifugal microfluidic device at the m wavelength bands by emitting from the plurality of light sources the m light beams having the m wavelength bands to the biochemical sample and sensing by the plurality of optical detectors intensities of the plurality of light beams that have passed through the biochemical sample and applying the m absorbances of the biochemical sample to the corresponding independent variables of the regression equation to calculate the concentration of the component in the biochemical sample.

16. The method of claim 15, wherein the biochemical sample is a diluted biochemical sample.

* * * * *